US008229556B2

(12) United States Patent  
Li

(10) Patent No.: US 8,229,556 B2  
(45) Date of Patent: Jul. 24, 2012

(54) TACHYCARDIA HEMODYNAMICS DETECTION BASED ON CARDIAC MECHANICAL SENSOR SIGNAL REGULARITY

(75) Inventor: Dan Li, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 314 days.

(21) Appl. No.: 12/283,185

(22) Filed: Sep. 10, 2008

(65) Prior Publication Data

US 2009/0131996 A1 May 21, 2009

Related U.S. Application Data

(60) Provisional application No. 61/003,905, filed on Nov. 21, 2007.

(51) Int. Cl.  
*A61N 1/39* (2006.01)

(52) U.S. Cl. .......................................................... 607/4

(58) Field of Classification Search ........................ 607/4  
See application file for complete search history.

(56) References Cited

U.S. PATENT DOCUMENTS

| 5,176,137 | A | * | 1/1993 | Erickson et al. .................. 607/4 |
| 6,221,011 | B1 | | 4/2001 | Bardy |
| 6,270,457 | B1 | | 8/2001 | Bardy |
| 6,277,072 | B1 | | 8/2001 | Bardy |
| 6,280,380 | B1 | | 8/2001 | Bardy |
| 6,312,378 | B1 | | 11/2001 | Bardy |
| 6,336,903 | B1 | | 1/2002 | Bardy |
| 6,358,203 | B2 | | 3/2002 | Bardy |
| 6,368,284 | B1 | | 4/2002 | Bardy |
| 6,398,728 | B1 | | 6/2002 | Bardy |
| 6,440,066 | B1 | | 8/2002 | Bardy |
| 7,336,994 | B2 | * | 2/2008 | Hettrick et al. .................. 607/5 |
| 2003/0014083 | A1 | * | 1/2003 | Kupper ............................ 607/9 |
| 2006/0122526 | A1 | * | 6/2006 | Berenfeld et al. ............. 600/515 |
| 2006/0122651 | A1 | * | 6/2006 | Whitman ........................ 607/14 |
| 2006/0161069 | A1 | * | 7/2006 | Li ................................ 600/515 |
| 2006/0281999 | A1 | * | 12/2006 | Li ................................ 600/518 |
| 2007/0049974 | A1 | * | 3/2007 | Li et al. ............................. 607/4 |
| 2007/0239218 | A1 | * | 10/2007 | Carlson et al. .................. 607/18 |

OTHER PUBLICATIONS

Papezova, S. Signal Processing of Bioimpedance Equipment. Sensors and Actuators. B 95 (2003) 328-335.*  
Schuckers et al. Arrhythmia Analysis, Automated. Encyclopedia of Medical Devices and Instrumentation. 2nd Edition (2006) 69-84.*  
Richman et al. Physiological time-series analysis using approximate entropy and sample entropy. Am J Physiol Heart Circ Physiol 278:H2039-H2049, 2000.*

* cited by examiner

*Primary Examiner* — Carl H Layno  
*Assistant Examiner* — Jeremiah Kimball  
(74) *Attorney, Agent, or Firm* — Hollingsworth Davis, LLC

(57) ABSTRACT

Systems and methods provide for sensing, within a patient and during an event of tachycardia, a signal indicative of a mechanical response of the patient's heart to the tachycardia. Regularity of the signal relative to a threshold established for the patient is determined. A state of patient hemodynamics during the tachycardia event is determined based at least in part on the regularity of the signal. One or more anti-tachycardia therapies to treat the tachycardia may be selected based at least in part on the determined state of patient hemodynamics. The selected one or more anti-tachycardia therapies may be delivered to treat the tachycardia.

25 Claims, 8 Drawing Sheets

TACHYCARDIA HEMODYNAMICS DETECTION BASED ON CARDIAC MECHANICAL SENSOR SIGNAL REGULARITY

RELATED APPLICATIONS

This application claims the benefit of Provisional Patent Application Ser. No. 61/003,905 filed on Nov. 21, 2007, to which priority is claimed pursuant to 35 U.S.C. §119(e) and which is hereby incorporated herein by reference in its entirety.

FIELD OF THE INVENTION

The present invention relates generally to evaluating patient hemodynamics, and more specifically, to assessing a patient's hemodynamic status during a tachycardia event based on regularity of a cardiac mechanical sensor signal.

BACKGROUND OF THE INVENTION

Proper cardiac function relies on the synchronized contractions of the heart at regular intervals. When normal cardiac rhythm is initiated at the sinoatrial node, the heart is said to be in sinus rhythm. However, when the heart experiences irregularities in its coordinated contraction, due to electrophysiologic disturbances caused by a disease process or from an electrical disturbance, the heart is denoted to be arrhythmic. The resulting cardiac arrhythmia impairs cardiac efficiency and can be a potential life threatening event.

Cardiac arrhythmias occurring in the atria of the heart, for example, are called supra-ventricular tachyarrhythmias (SVTs). SVTs take many forms, including atrial fibrillation and atrial flutter. Both conditions are characterized by rapid, uncoordinated contractions of the atria. Besides being hemodynamically inefficient, the rapid contractions of the atria can also adversely effect the ventricular rate. This occurs when the aberrant contractile impulse in the atria are transmitted to the ventricles. It is then possible for the aberrant atrial signals to induce ventricular tachyarrhythmias.

Cardiac arrhythmias occurring in the ventricular region of the heart, by way of further example, are called ventricular tachyarrhythmias. Ventricular tachycardia (VTs), for example, are conditions denoted by a rapid heart beat, 150 to 250 beats per minute, that has its origin in some abnormal location with the ventricular myocardium. The abnormal location typically results from damage to the ventricular myocardium from a myocardial infarction. Ventricular tachycardia can quickly degenerate into ventricular fibrillation (VF). Ventricular fibrillation is a condition denoted by extremely rapid, non synchronous contractions of the ventricles. This condition is fatal unless the heart is returned to sinus rhythm within a few minutes.

Implantable cardioverter/defibrillators (ICDs) have been used as an effective treatment for patients with serious ventricular tachyarrhythmias. ICDs are able to recognize and treat tachyarrhythmias with a variety of therapies. To effectively deliver these treatments, the ICD must first identify the type of tachyarrhythmia that is occurring, after which appropriate therapy may be provided to the heart. An inaccurate identification of a detected tachyarrhythmia by the ICD can result in delivery of a high energy therapy, such as defibrillation therapy, when such therapy is unnecessary and undesirable.

SUMMARY OF THE INVENTION

The present invention is generally directed to systems and methods for evaluating patient hemodynamics. Systems and methods of the present invention are directed to assessing a patient's hemodynamic status during a tachycardia event based on regularity of a cardiac mechanical sensor signal. Systems and methods of the present invention are further directed to delivering appropriate cardiac electrical therapy in response to a patient's hemodynamic status during a tachycardia event detected based on regularity of a cardiac mechanical sensor signal.

According to various embodiments, methods of the present invention involve sensing, within a patient and during an event of tachycardia, a signal indicative of a mechanical response of the patient's heart to the tachycardia. Regularity of the signal relative to a threshold established for the patient is determined. A state of patient hemodynamics during the tachycardia event is determined based at least in part on the regularity of the signal. One or more anti-tachycardia therapies to treat the tachycardia may be selected based at least in part on the determined state of patient hemodynamics. The selected one or more anti-tachycardia therapies may be delivered to treat the tachycardia.

In accordance with various embodiments, methods of the present invention involve sensing, within a patient and during an event of tachycardia, a signal indicative of a mechanical response of the patient's heart to the tachycardia, and determining a metric indicative of regularity of the signal relative to one or more thresholds established for the patient. Embodiments further involve quantizing the regularity metric into one of a plurality of discrete levels of hemodynamic stability for assessing a state of patient hemodynamics during the tachycardia event.

According to further embodiments, implantable systems include an implantable cardiac mechanical sensor configured to produce a signal indicative of a mechanical response of a patient's heart to an event of tachycardia. A lead comprising one or more electrodes and is coupled to detection circuitry and energy delivery circuitry. A processor is coupled to the sensor, lead, detection circuitry, and energy delivery circuitry. The processor is configured to receive the signal during the tachycardia event, determine regularity of the signal relative to a threshold established for the patient, and determine a status of patient hemodynamics during the tachycardia event based at least in part on the regularity of the signal. The processor is configured to deliver one or more anti-tachycardia therapies associated with the hemodynamic status of the patient.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
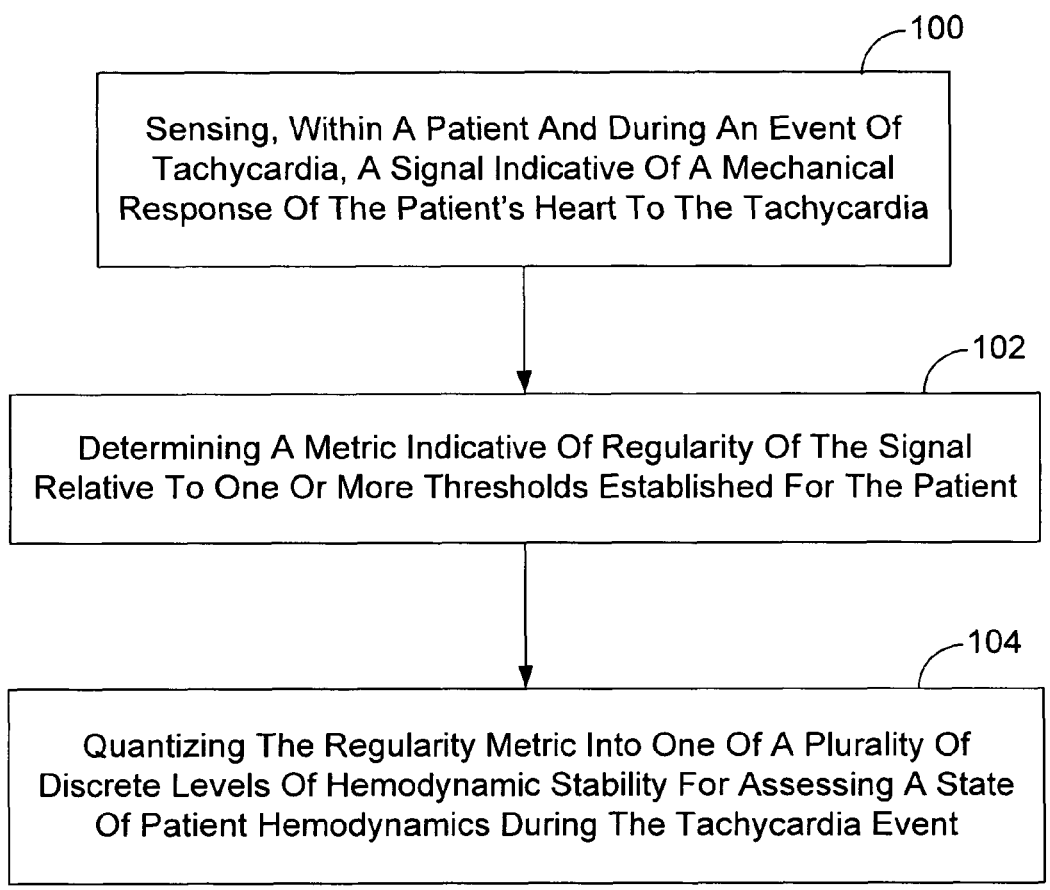
FIG. 1 is a flow diagram showing various processes involving assessment of patient hemodynamics in accordance with embodiments of the present invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings, which form a part hereof, and in which is shown by way of illustration, various embodiments in which the invention may be practiced. It is to be understood that other embodiments may be utilized, and structural and functional changes may be made without departing from the scope of the present invention.

Systems, devices or methods according to the present invention may include one or more of the features, structures, methods, or combinations thereof described hereinbelow. For example, a device or system may be implemented to include one or more of the features and/or processes described below. It is intended that such device or system need not include all of the features described herein, but may be implemented to include selected features that provide for useful structures and/or functionality. Such a device or system may be implemented to provide a variety of therapeutic or diagnostic functions.

In some configurations, devices or systems of the present invention may be configured for intrathoracic or transvenous deployment or a combination thereof. In other configurations, devices or systems of the present invention may be implanted subcutaneously, but extra-thoracically. In further configurations, systems and devices of the present invention may include some or all components that are configured for cutaneous or patient-external deployment, such as in diagnostic configurations. Accordingly, a wide range of device and system configurations are contemplated.

Delivering the appropriate therapy when needed to treat a cardiac arrhythmia is an important function of an implantable cardiovertor/defibrillator (ICD). To determine the "appropriateness" of a therapy to treat an arrhythmia, an ICD requires accurate and immediate interpretation of the arrhythmia and assessment of patient hemodynamic status. During the arrhythmia, there is change in cardiac synchrony. It is expected that hemodynamically stable and unstable arrhythmias have different levels of impact on cardiac synchrony. Detecting and quantifying the change in cardiac synchrony may help to gauge the hemodynamic outcome during arrhythmia.

Embodiments of the present invention are directed to systems and methods that provide for hemodynamics detection during tachycardia. Embodiments of the present invention provide for hemodynamic stability detection using one or more implantable sensors that detect the mechanical function of the heart during tachycardia. In particular, detecting cardiac mechanical function during tachycardia is based on the sensor signal regularity. It is believed that, during hemodynamically stable tachycardia, cardiac mechanical sensor signals are more regular or organized as compared to those acquired during hemodynamically unstable tachycardias. A more regular sensor signal is believed to be a reflection of a higher degree of cardiac synchrony, which would result in better cardiac output. Typical mechanical sensors that may be employed in accordance with the present invention include those configured for sensing blood pressure, blood flow, cardiac wall motion, contractility, heart sound, or indirect measures such as impedance or other surrogates or cardiac mechanical function.

Embodiments of the present invention advantageously exploit signal regularity to evaluate the hemodynamic status of a patient during arrhythmias using one or more cardiac mechanical sensors. This technique differs from conventional methods in two important aspects. First, most conventional approaches focus on beat-by-beat feature extraction from a raw waveform (time series) or of the transformed signals such as in the frequency domain. Examples of these features include signal peak, peak-trough value, slope, and waveform integral. According to embodiments of the present invention, beat-wise feature extraction is replaced by an evaluation of the overall signal regularity over time. If the signal is very regular (e.g., similar morphology over time), then this indicates an organized synchrony when the arrhythmia occurs, and the cardiac function is not severely compromised. In this case, the arrhythmia is deemed well tolerated.

Second, use of signal regularity for arrhythmia classification has been reported, but is focused on the use of ECG or intracardiac electrograms to indicate how organized the electrical activation is during arrhythmia. Embodiments of the present invention consider the organization of the mechanical cardiac function during arrhythmia, which is a direct representation of the hemodynamic outcome of the arrhythmia.

FIG. 1 is a flow diagram showing various processes involving assessment of patient hemodynamics in accordance with embodiments of the present invention. According to FIG. 1, embodiments of the present invention involve sensing 100, within a patient and during an event of tachycardia, a signal indicative of a mechanical response of a patient's heart to the tachycardia. A metric indicative of regularity of the signal relative to one or more thresholds established for the patient is determined 102. The method further involves quantizing 104 the regularity metric into one of a multiplicity of discrete levels of hemodynamic stability for assessing a state of patient hemodynamics during the tachycardia event.

Figure 2:
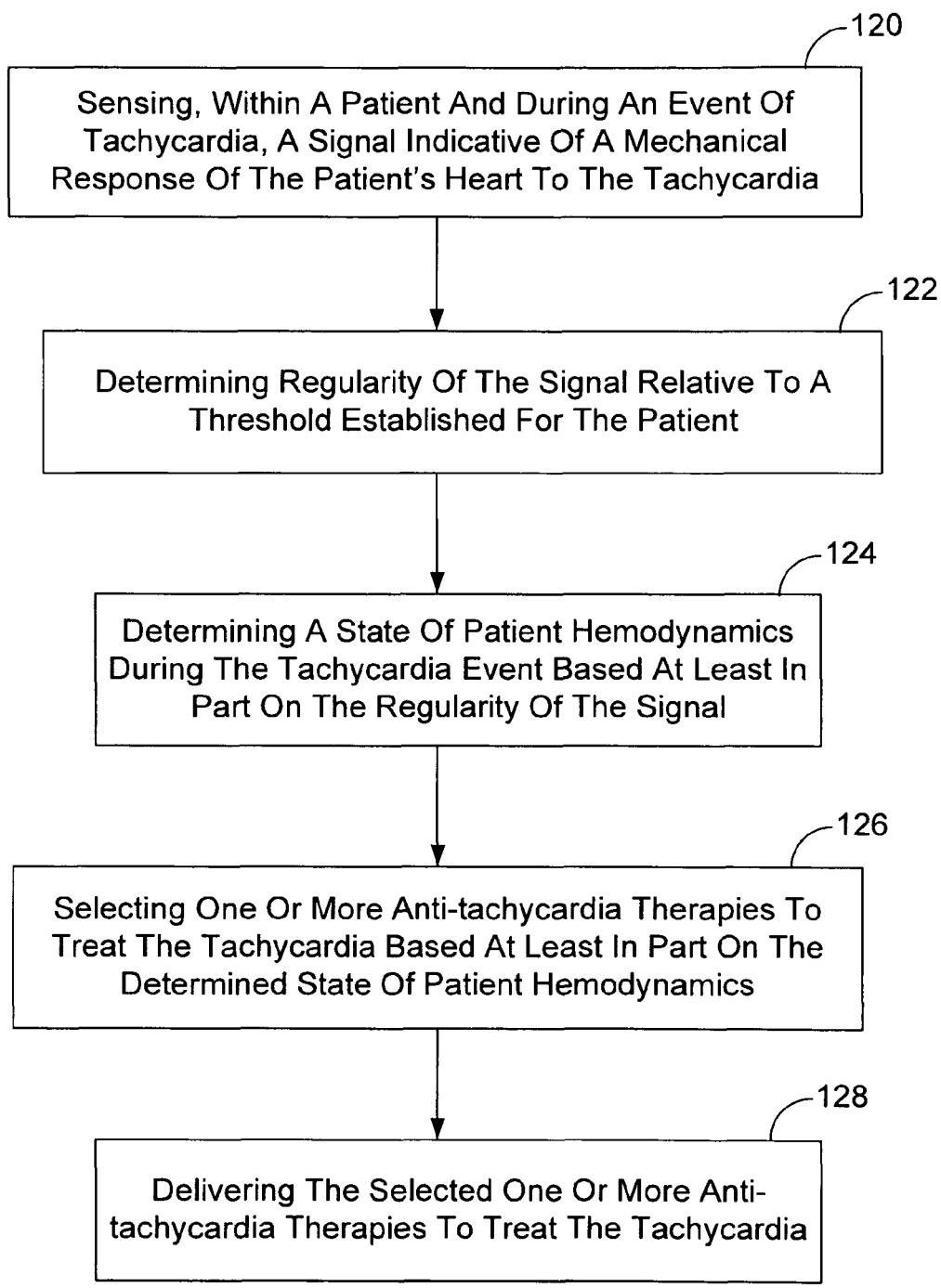
FIG. 2 is a flow diagram showing various processes involving assessment of patient hemodynamics in accordance with other embodiments of the present invention.

FIG. 2 is a flow diagram showing various processes involving assessment of patient hemodynamics in accordance with other embodiments of the present invention. According to FIG. 2, embodiments of the present invention involve sensing 120, within a patient and during an event of tachycardia, a signal indicative of a mechanical response of the patient's heart to the tachycardia and determining 122 regularity of the signal relative to a threshold established for the patient.

Embodiments according to FIG. 2 further provide for determining 124 a state of patient hemodynamics during the tachycardia event based at least in part on the regularity of the signal. One or more anti-tachycardia therapies to treat the tachycardia may be selected 126 based at least in part on the determined state of patient hemodynamics. The selected one or more anti-tachycardia therapies may then be delivered 128 to treat the tachycardia.

Embodiments of the present invention are directed to different aspects of mechanical cardiac function during the arrhythmia, which can be sensed directly or indirectly using various types of sensors. These different aspects and types of sensors may be implemented individually or in various combinations. For example, some embodiments may employ a single sensor configured to sense one or more aspects of mechanical cardiac function during the arrhythmia. In other embodiments, multiple sensors may be used, each configured to sense one or more of the same or different aspects of mechanical cardiac function during the arrhythmia.

In some configurations, for example, an intracardiac pressure sensor may be configured and used to sense an intracardiac pressure change, volume change, cardiac contractility, cardiac relaxation, or wall motion. In other configurations, an intravascular pressure sensor may be configured and used to sense a pressure change or a volume change, thus providing estimates of the variation of cardiac output. According to further configurations, accelerometers, microphones, or other heart sounds sensors may be configured and used to sense heart sounds, which may produce an output that is a reflection of A-V synchrony and hemodynamics during tachycardia. In still other configurations, various types of impedance sensors may be configured and used to sense transthoracic impedance, intracardiac impedance, or intra-myocardial impedance change as a result of volume change or perfusion compromise during tachyarrhythmia. Other useful sensors include blood chemistry sensors, for example.

A cardiac mechanical sensor of the present invention can be deployed across the chest (externally or, more preferably, internally), implanted through the cardiovascular system or embedded subcutaneously. Cardiac mechanical sensors of the present invention can be configured to communicate with a control device, such as an ICD, for data and/or command interchange via a wired or wireless link.

Signal regularity can be evaluated using a variety of methods. Regularity of a cardiac mechanical signal may be measured against a threshold established for a particular patient or from a population of patients. According to one approach, a template matching or correlation method may be used. For example, a template may be generated that incorporates cardiac mechanical sensor signals within one or more beats acquired during a tachyarrhythmia. A variety of templates may be generated for various types of tachyarrhythmias. For example, one or more templates may be generated for ventricular tachycardia (VT), different types of ventricular tachycardia (VT-1, VT-2), and ventricular fibrillation (VF), for example.

The template may then be compared to a cardiac mechanical sensor signal acquired during an event of tachycardia to determine regularity of the sensor signal. Various methodologies may be employed to perform the template-sensor signal comparison and generate similarity scores for a series of consecutive beats. For example, morphological features extracted from the template and the morphological features extracted from the sensor signals during each cardiac cycle may be fed into a feature correlation coefficient (FCC) calculator, which yields the similarity scores (FCC) for all the beats. Variance of these similarity scores indicates how consistently the sensor signal under investigation correlates to the template. A large variance indicates less consistency, therefore low regularity of the sensor signal, and vice versa. A threshold can be chosen for the variance of the similarity scores to make the decision of regular or irregular sensor signal.

Determining signal regularity according to other approaches may be accomplished using frequency domain analysis, such as power spectral analysis. For example, the width or change of the width of the dominant spectral peak of the signal may indicate the complexity of the signal in terms of richness of frequency contents. A power spectrum with multiple peaks, for example, suggests rich frequency contents. A narrow and sharp dominant spectral peak, and/or significant "dominance" of the dominant spectral peak (indicated by, for example, larger ratio between the dominant spectral peak amplitude and the second dominant spectral peak amplitude) are indications of increased regularity of the signal.

Singular value decomposition may be used to determine cardiac mechanical signal regularity in accordance with other approaches. For example, techniques such as the principle component analysis or independent component analysis may disclose the dominance of the major component. The spread of the eigenvalues or singular values indicates elevated irregularity of the signal or complexity of the system.

Entropy based methods may also be used in accordance with other approaches. An approximate or sample entropy that gives the conditional probability estimate of the system to be predictable, or regular, may be used. For example, a sample entropy technique may be used to determine cardiac mechanical signal regularity. A larger entropy estimate indicates higher irregularity, and vise versa. Sample entropy is computed as the negative natural logarithm of the conditional probability of the signal under investigation being self-similar. This conditional probability ranges between 0 and 1, where 1 indicates that the signal under investigation is very well organized or regular, whereas 0 indicates that the signal under investigation is totally chaotic (i.e. irregular).

Although different signal regularity determination techniques are described herein, it is understood that two or more of these techniques may be used in combination. Using two or more different signal regularity determination techniques may provide for an increased level of accuracy when evaluating a cardiac mechanical signal for regularity.

Cardiac mechanical sensor signal regularity can be use to detect, or track (in a continuous monitor mode), the hemodynamic status of a patient during arrhythmia. In one embodiment, one or more threshold values are used to quantize a metric of signal regularity into a number of discrete levels of hemodynamic stability. These discrete levels may be established to delineate between stable and unstable hemodynamic states, and for different levels of these states.

For example, the signal regularity from a hemodynamic sensor can be quantized into three levels using two distinct "regularity thresholds," Th1 and Th2, representing "high regularity," "medium regularity," and "low regularity." High regularity indicates very stable hemodynamics, low regularity indicates very unstable hemodynamics, and the medium regularity indicates somewhat blunted hemodynamics during arrhythmia. By way of example, for the signal regularity computed using the sample entropy method, by thresholding the conditional probability (Pr), the three regularity levels can be defined as High if $1<=Pr<0.8$, Medium if $0.8<=Pr<=0.4$, and Low if $0<=Pr<0.4$. Reference to a baseline value (i.e. during normal sinus rhythm) in establishing a threshold is important because it sets the "normal" values for a specific patient with his/her specific sensor deployment or configuration.

After a hemodynamic status level is determined, an anti-arrhythmic therapy associated with that hemodynamic status during arrhythmia can be delivered. In one embodiment, if the detected tachycardia is deemed hemodynamically stable, then anti-tachycardia pacing (ATP) can be delivered, and/or the arrhythmia sustained duration timer can be extended. Various forms of ATP therapy that differ in terms of aggressiveness may be selected for delivery based on the relative degree of hemodynamic stability (e.g., ATP-1 for treating tachyarrhythmias of relatively high stability, ATP-2 for treating tachyarrhythmias of relatively low stability, where ATP-2 is more aggressive than ATP-1). Otherwise, defibrillation therapy can be immediately delivered once the arrhythmia is declared hemodynamically unstable.

Assessing patient hemodynamics based on cardiac mechanical signal regularity in accordance with the present invention can also be used post therapy to evaluate whether the therapy delivered to the patient was effective in recovering patient hemodynamics. By using hemodynamic status tracking according to the present invention, the implantable device can decide whether another therapy is needed or would be more effective if it is determined that the regularity value is not recovering to a "normal" value within a certain time duration.

As previously discussed, a variety of different sensors that measure cardiac mechanical function may be used in connection with a cardiac mechanical signal regularity determination approach in accordance with the present invention. Systems and methods of the present invention may employ a broad scope of sensor modalities and sensor signals.

Heart sounds sensors, for example, are well suited for use in performing hemodynamic status assessments in accordance with the present invention. Suitable heart sounds sensors include accelerometers that sense vibrations and microphones that sense sound pressure levels, from which a heart sounds signal may be extracted, typically through some preprocessing techniques such as bandpass filtering or source separation. A heart sounds sensor may be implemented as an in-can or on-can accelerometer, for example.

Other suitable sensors include various types of pressure sensors that provide a cardiac mechanical output signal, typically through filtering. Useful pressure sensors include a lead-based (RV or LV) pressure sensor or a wireless pulmonary arterial (PA) pressure sensor, for example.

Still other suitable cardiac mechanical sensors include various types of cardiac impedance sensors, including those that provide for cardiac impedance (Z) vectors such as an RV tip-to-coil vector and an LV tip-to-can vector. Mixed sensors may be used, such as one acoustic or motion sensor (e.g., accelerometer) and one cardiac impedance sensor. A myriad of sensor and sensor signals, and combinations thereof, are contemplated.

Figure 3:
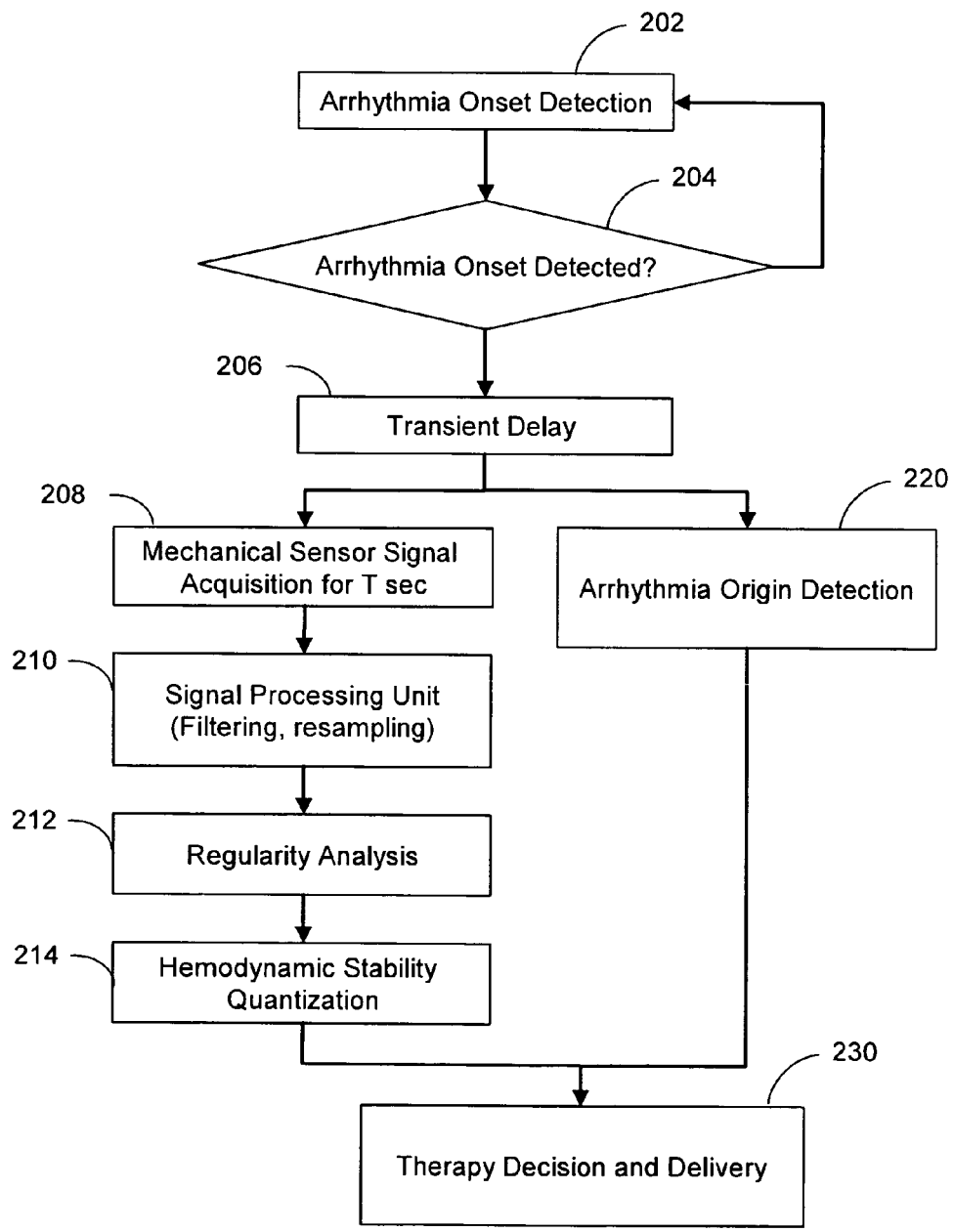
FIG. 3 is a flow diagram showing various processes involving hemodynamic stability detection and anti-arrhythmia therapy delivery in accordance with embodiments of the present invention.

FIG. 3 is a flow diagram showing various processes involving hemodynamic stability detection and anti-arrhythmia therapy delivery in accordance with embodiments of the present invention. According to this illustrative example, an arrhythmia onset is detected 202, 204, followed by a brief delay period 206. This delay period is preferably sufficiently long in duration to confirm a sustained tachycardia condition and to bypass transient hemodynamic instability associated with transient turbulence of the cardiac mechanical sensor signal. This delay period varies with the type of sensor used, but is typically in the range of about 500 ms to about 1500 ms.

Following this transient delay period 206, the cardiac mechanical sensor signal of duration T is acquired 208. It is noted that the cardiac mechanical sensor may be activated within a patient to collect physiologic data when certain events occur (event triggered) or when a command is issued (command triggered). As previously discussed, the acquired sensor signal may be subject to signal processing 210, such as filtering and/or resampling.

The cardiac mechanical sensor signal is subject to regularity analysis 212, preferably in accordance with the methodologies previously discussed. For example, the cardiac mechanical sensor signal may be subject to sample entropy analysis. Hemodynamic stability is then determined 214 based on regularity of the cardiac mechanical sensor signal, preferably in a manner described hereinabove.

As is further shown in FIG. 3, the origin of the arrhythmia is determined 220. Various techniques may be used to determine whether the arrhythmia is of atrial origin (e.g., supraventricular tachycardia) or of ventricular origin (e.g., VT or VF). These techniques include, but are not limited to, analyzing the RR intervals and determining the arrhythmia rate, rate stability, suddenness of the onset (i.e., acceleration of heart rate), atrial and ventricular heart rate relationship; or analyzing the morphologies of the intracardiac electrograms and determining the morphological similarities between a template (acquired during normal sinus rhythm) and during arrhythmias.

The hemodynamic information and arrhythmia origin information is communicated to a therapy decision and delivery block 230, where an appropriate therapy is selected, from a number of pre-programmed therapies, or modified, from an existing or programmed therapy, and delivered. For example, ATP therapy may be delivered for stable arrhythmias, and defibrillation therapy may be immediately delivered for unstable arrhythmias.

To enhance the quality of the cardiac mechanical signal and reduce computational burden, it may be desirable to employ a preprocessing unit. The preprocessing unit may provide for band-limit filtering of the cardiac mechanical signal to obtain the component of interest, compute a profile, such as the Shannon energy envelop of the cardiac mechanical signal, and/or down sample the cardiac mechanical signal data.

The following is an illustrative example of hemodynamic stability assessment in accordance with embodiments of the present invention that uses a heart sounds sensor. This illustrative example summarizes a preclinical animal (swine) study in which an accelerometer was used to detect and record a heart sounds (HS) signal. The opening and closing of the patient's heart valves during a heartbeat causes high-frequency vibrations in the adjacent heart wall and blood vessels. These vibrations can be sensed in the patient's body as heart sounds, and may be detected by sensors. A phonocardiogram (PCG) transducer, for example, may be implanted within a patient and converts acoustical energy of the heart sounds to electrical energy, resulting in a PCG waveform 120 that may be recorded, processed, and/or displayed, as shown by the graph in the upper portion of FIG. 4.

Figure 4:
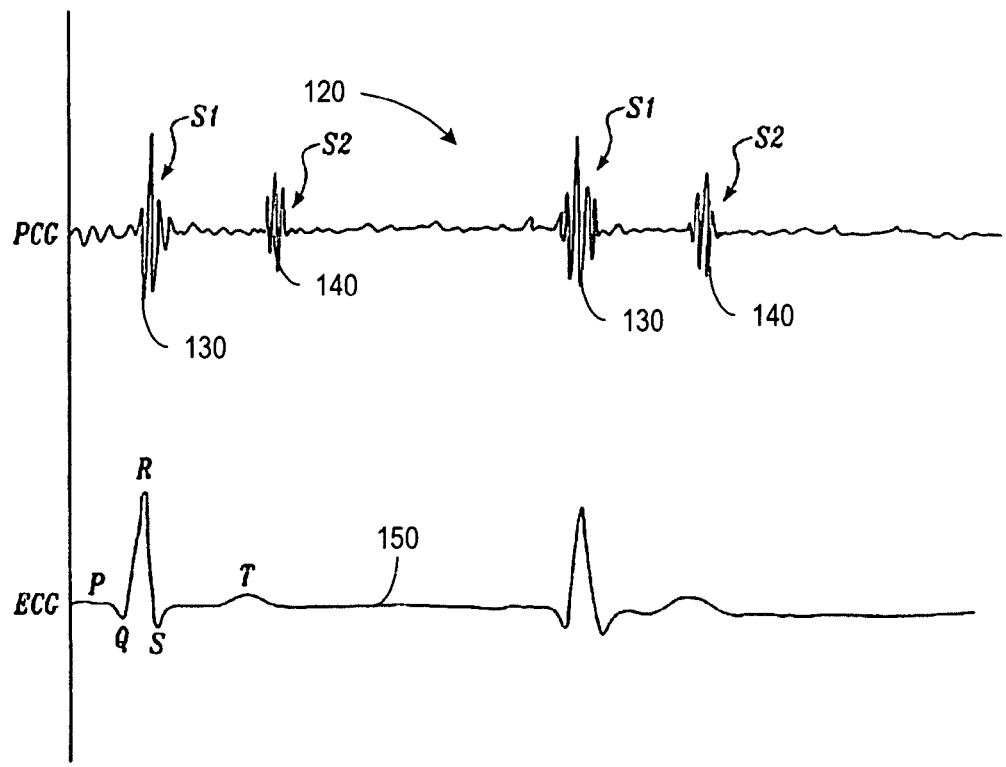
FIG. 4 is a pictorial diagram of a phonocardiogram (PCG) waveform and an electrocardiogram (ECG) waveform for two consecutive heartbeats.
Figure 5A:
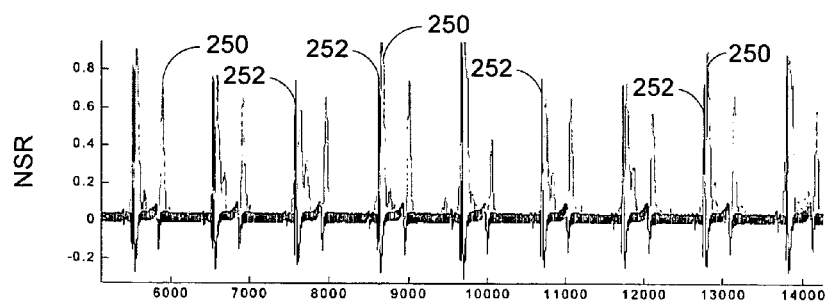
FIGS. 5A-5D show a Shannon energy profile of a heart sounds recording signal obtained from a surface accelerometer for each of four test subjects and an EGM signal obtained from a right ventricular lead electrode for each of four cardiac scenarios, including normal sinus rhythm, stable ventricular tachycardia, unstable ventricular tachycardia, and ventricular fibrillation.
Figure 5B:
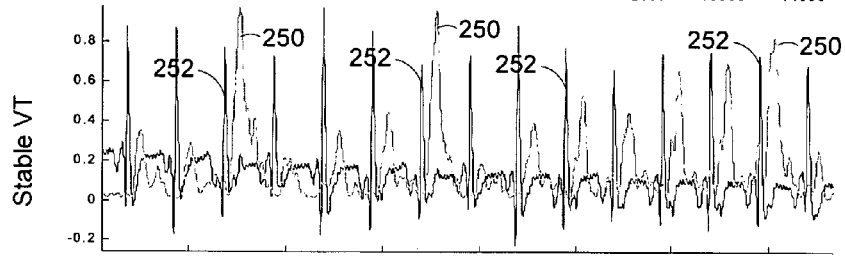
Figure 5C:
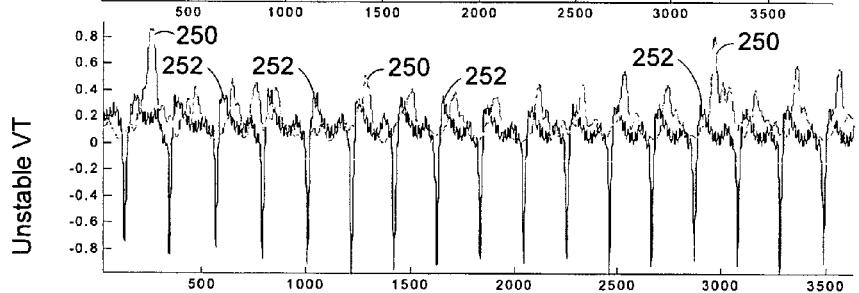
Figure 5D:
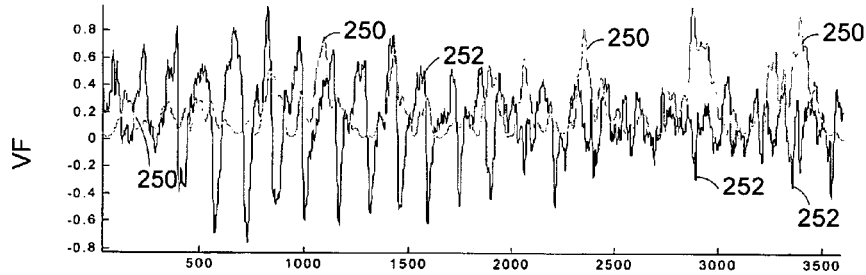

As indicated by the PCG waveform 120 shown in FIG. 4, a typical heartbeat produces two main heart sounds. A first heart sound 130, denoted S1, is generated by vibration generally associated with the closure of the tricuspid and mitral valves at the beginning of systole. Typically, the heart sound 130 is about 14 milliseconds long and contains frequencies up to approximately 500 Hz. A second heart sound 140, denoted S2, is generally associated with vibrations resulting from the closure of the aortic and pulmonary valves at the end of systole. While the duration of the second heart sound 140 is typically shorter than the first heart sound 130, the spectral bandwidth of the second heart sound 140 is typically larger than that of the first heart sound 130.

An electrocardiogram (ECG) waveform 150 describes the electrical activity of a patient's heart. The graph in the lower portion of FIG. 4 illustrates an example of the ECG waveform 150 for two heartbeats and corresponds in time with the PCG waveform 120 also shown in FIG. 4. Referring to the first shown heartbeat, the portion of the ECG waveform 150 representing depolarization of the atrial muscle fibers is referred to as the "P" wave. Depolarization of the ventricular muscle fibers is collectively represented by the "Q," "R," and "S" waves of the ECG waveform, referred to as the QRS complex. Finally, the portion of the waveform 150 representing repolarization of the ventricular muscle fibers is known as the "T" wave. Between heartbeats, the ECG waveform 150 returns to an isopotential level.

According to this preclinical swine study example, a surface accelerometer was used to record the heart sounds (HS) signals concurrently with EGMs and intracardiac pressures during induced VT and VF episodes. The sample entropy method discussed above was used to determine the HS signal regularity, which is a number between 0 and 1, with 1 indicating the signal to be very well organized and 0 totally chaotic. The heart signal used in the analysis was acquired 1.5-2 seconds after the VT/VF onset, and the duration of the HS data segment was 10 cardiac cycles. Heart sounds signal regularity during NSR was also computed. For induced VT episodes, heart sounds signal regularity was further separated into hemodynamically stable and unstable VT using the following definition. If the mean aortic pressure (MAoP) during the first 2 seconds of VT is >50% of the baseline MAoP, then this VT episode was considered hemodynamically stable. Otherwise, this VT episode was considered hemodynamically unstable.

An example of the heart sounds recordings from the surface accelerometer during NSR, stable VT, unstable VT, and VF are provided in FIGS. 5A-5D, respectively. FIGS. 5A-5D show a Shannon energy profile 250 of the heart sounds recording signal obtained from a surface accelerometer for each of four test subjects. Also shown is an EGM signal 252 obtained from a right ventricular lead electrode. FIGS. 5A-5D pictorially demonstrate how the regularity of the heart sounds signal 250 progressively deteriorates (moving from highly organized to chaotic) as the cardiac rhythms progress from NSR to VF.

Figure 6:
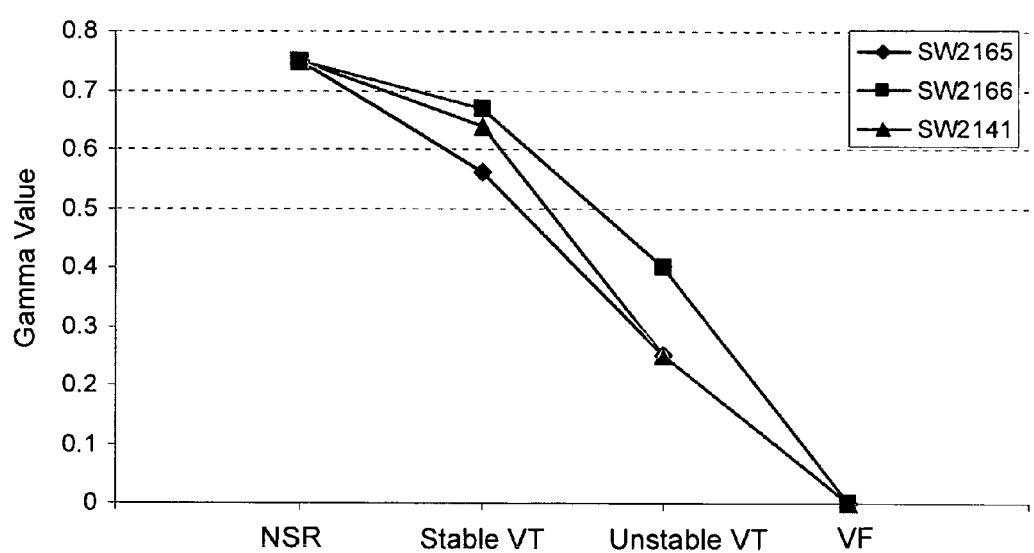
FIG. 6 is a plot of gamma values of heart sounds signal acquired during NSR, stable VT, unstable VT, and VF.

FIG. 6 is a plot of gamma values of the heart sounds signal acquired during NSR, stable VT, unstable VT, and VF. It is noted that the negative logarithm of the gamma values gives the sample entropy. The gamma values of 10-beat heart sounds signal segments were obtained from three animals in this illustrative example. FIG. 6 demonstrate that the heart sounds signal becomes progressively unorganized or non-regular as the arrhythmia progresses in severity from stable VT to VF. A clear decrease of gamma value can be seen as the arrhythmia becomes hemodynamically unstable. With more episodes and more animals from the study being analyzed, accumulative results clearly demonstrate that gamma value is statistically smaller during unstable VT and VF, compared to stable VT.

A hemodynamic status assessment methodology of the present invention may be implemented in a variety of medical diagnostic devices and systems, including implantable and patient-external devices and systems. For example, a hemodynamic status assessment methodology of the present invention may be implemented entirely by an implanted device (e.g., pacemaker, ICD, CRT device, cardiac monitoring device), entirely by a patient-external system, or in a distributed manner by both implanted and patient-external devices or systems. In the context of a patient-external or distributed approach, various external systems may be employed, such as a programmer and/or a networked system, such as an advanced patient management system.

Figure 7:
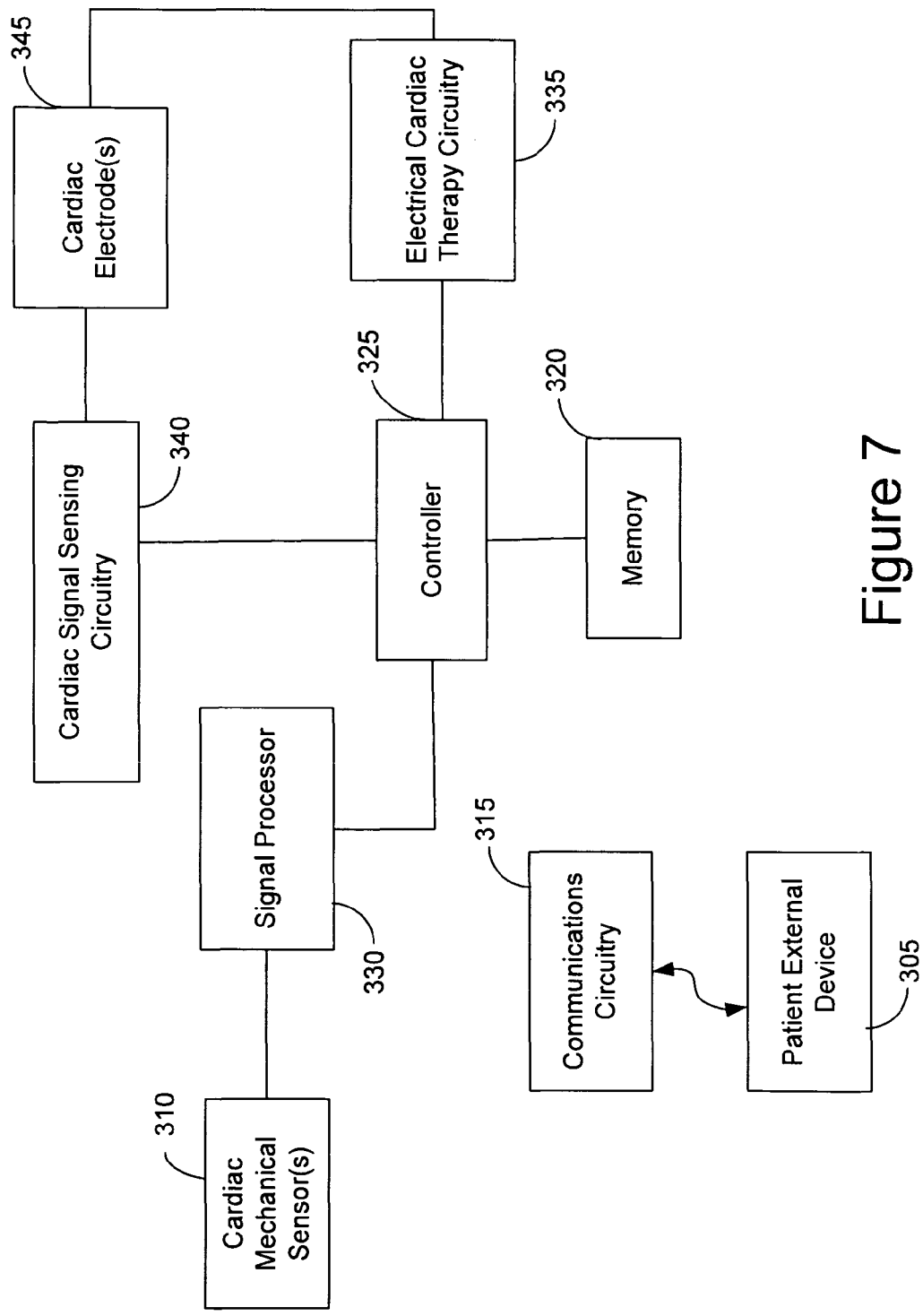
FIG. 7 is a block diagram of circuitry that implements a hemodynamic status assessment methodology in accordance with embodiments of the invention.

FIG. 7 is a block diagram of circuitry that implements a hemodynamic status assessment methodology in accordance with embodiments of the invention. One or more cardiac electrodes 345 may be positioned or disposed at multiple locations on, within, or proximate a heart chamber or vasculature. For example, one or more cardiac leads may support one or more the cardiac electrodes, and the can or housing of the device may include one or more electrodes useful for sensing cardiac electrical activity (and may also serve as an electrode for energy delivery).

One or more cardiac mechanical sensors 310 are configured to sense a mechanical function of the heart, and may be the same or different sensor type or sensing modality, as discussed previously. Signals produced by the one or more sensors 310 may be communicated to a signal processor 330, which processes the sensor signals for use by a controller 325.

The controller 325 is coupled to the signal processor 330, memory 320, and cardiac signal sensing circuitry 340. In some embodiments, hemodynamic status may be evaluated in accordance with the present invention in a monitoring mode or configuration, in which case electrical cardiac therapy circuitry 335 need not be included. In this regard, embodiments of the present invention may be directed to a diagnostic device that incorporates one or more cardiac mechanical sensors. In other embodiments that provide cardiac electrical therapy, hemodynamic status may be evaluated during arrhythmias and appropriate therapy delivered according to the hemodynamic stability of the arrhythmia using cardiac electrical circuitry 335 in accordance with the present invention.

The memory 320 is configured to store program instructions and/or data. In addition, the stored information may be used to provide a log of events for display or analysis at a later time. The memory 320 may be configured to store one or more thresholds for determining sensor signal regularity and/or quantizing a signal regularity measure into discrete levels of hemodynamic stability, such as in accordance with the algorithm shown in FIG. 3. Alternatively, these thresholds may be stored in the memory of a patient-external device or system, and an external controller may be used to perform hemodynamic stability assessments.

The controller 325 is preferably coupled to communications circuitry 315 which allows the device to communicate with other devices 305, such as a patient-external programmer or advanced patient management system. In some implementations, an advanced patient management (APM) system may be used to collect implanted device data, including cardiac mechanical sensor data, for purposes of evaluating the hemodynamic status of a patient. The APM system or programmer may also be used to implement or facilitate implementation of the hemodynamic status assessment methodology of the present invention. Methods, structures, and/or techniques described herein, may incorporate various APM related methodologies, including features described in one or more of the following references: U.S. Pat. Nos. 6,221,011; 6,270,457; 6,277,072; 6,280,380; 6,312,378; 6,336,903; 6,358,203; 6,368,284; 6,398,728; and 6,440,066, which are hereby incorporated herein by reference.

Figure 8:
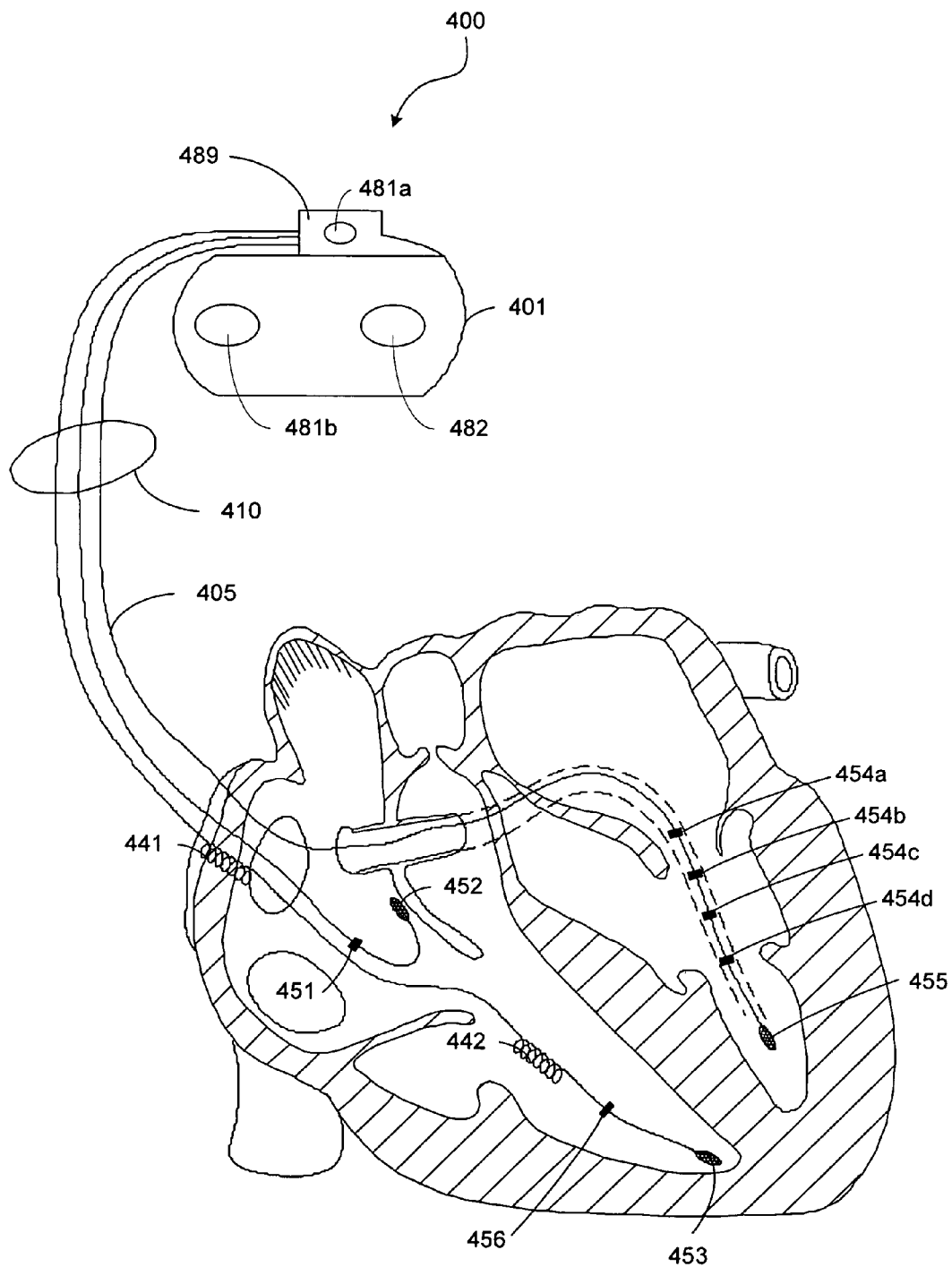
FIG. 8 illustrates a patient-implantable device that may be used in conjunction with a hemodynamic status assessment methodology in accordance with embodiments of the present invention.

FIG. 8 shows an embodiment of the present invention implemented with use of an implanted cardiac therapy device 400. The therapy device 400 includes cardiac rhythm management circuitry enclosed within an implantable housing 401. The CRM circuitry is electrically coupled to an intracardiac lead system 410. Portions of the intracardiac lead system 410 are shown inserted into the patient's heart. The lead system 410 includes cardiac pace/sense electrodes 451-456 positioned in, on, or about one or more heart chambers for sensing electrical signals from the patient's heart and/or delivering pacing pulses to the heart. The intracardiac sense/pace electrodes 451-456 may be used to sense and/or pace one or more chambers of the heart, including the left ventricle, the right ventricle, the left atrium and/or the right atrium. The lead system 410 may include one or more defibrillation electrodes 441, 442 for delivering defibrillation/cardioversion shocks to the heart.

The left ventricular lead 405 incorporates multiple electrodes 454a-454d positioned at various locations within, on or about the left ventricle. Stimulating the ventricle at multiple locations or at a single selected location may provide for increased cardiac output in a patients suffering from HF. In accordance with various embodiments described herein, one or more of the electrodes 454a-454d are selected for pacing the left ventricle. In other embodiments, leads having multiple pacing electrodes positioned at multiple locations within a chamber, such as the one illustrated by the left ventricular lead 405 of FIG. 10, may be implanted within any or all of the heart chambers. A set of electrodes positioned within one or more chambers may be selected. Electrical stimulation pulses may be delivered to the chambers via the selected electrodes according to a timing sequence and output configuration that enhances cardiac function.

Portions of the housing 401 of the implantable device 400 may optionally serve as one or multiple can or indifferent electrodes. The housing 401 is illustrated as incorporating a header 489 that may be configured to facilitate removable attachment between one or more leads and the housing 401. The housing 401 of the therapy device 400 may include one or more can electrodes 481b. The header 489 of the therapy device 400 may include one or more indifferent electrodes 481a.

The housing 401 and/or header 489 may include one or more cardiac mechanical sensors 482, such as an accelerometer or microphone configured for heart sound sensing. One or more cardiac leads 410 or separate sensor leads may incorporate one or more cardiac mechanical sensors, such as a pulmonary arterial pressure sensor.

In accordance with a further embodiment, a separate heart sounds monitor may be implanted and coupled to one or more heart sounds sensors and the header 489 of the housing 401. The coupling between the heart sounds monitor and the implantable device 400 may be effected through wired or wireless connectivity. The heart sounds monitor may include a processor and other circuitry that implements hemodynamic status assessment in accordance with present invention. The heart sounds monitor may communicate assessment data to the implanted device 400 which may implement an appropriate therapy. In such a configuration, a previously implanted CRM device 400 may be effectively upgraded, with appropriate software updates, to allow for therapy delivery based at least in part on hemodynamic status assessments made by a later-implanted heart sounds monitor in accordance with the present invention.

It is noted that a separate heart sounds monitor and/or heart sounds sensors may be configured for cutaneous or patient-external deployment, and may communicate with the implanted device 400 or a patient-external system via a wireless link. It is further noted that the heart sounds sensors may be configured for external or internal deployment with or without the need of heart sounds monitor. In such a configuration, each of the heart sounds sensors incorporate processing, memory, power, and communications circuitry to facilitate an independent heart sounds sensing capability. Heart sounds data acquired by the independent heart sounds sensors may be wirelessly communicated to the implanted device 400 or a patient-external system, such as a programmer or advanced patient management system, which may implement hemodynamic status assessment algorithms in accordance with the present invention.

The cardiac electrodes and/or other sensors disposed within or on the housing 401 or lead system 410 of the therapy device 400 may produce signals useful for detection and/or measurement of various physiological parameters, such as transthoracic impedance, respiration rate, minute ventilation, heart rate, cardiac dysynchrony, activity, posture, blood chemistry, O2 saturation, heart sounds, wall stress, wall strain, hypertrophy, inter-electrode impedance, electrical delays (PR interval, AV interval, QRS width, etc.), activity, cardiac chamber pressure, cardiac output, temperature, heart rate variability, depolarization amplitudes, depolarization timing, and/or other physiological parameters. It is contemplated that, in certain embodiments, information derived from such signals may be incorporated into the algorithm that is employed to assess hemodynamic status and deliver appropriate therapy based on same.

In some configurations, the implantable device 400 may incorporate one or more transthoracic impedance sensors that may be used to acquire the patient's respiratory waveform, and/or to acquire other respiratory-related information. The transthoracic impedance sensor may include, for example, one or more intracardiac electrodes 441, 442, 451-456 positioned in one or more chambers of the heart. The intracardiac electrodes 441, 442, 451-456 may be coupled to impedance drive/sense circuitry positioned within the housing 401 of the therapy device 400. Information from the transthoracic impedance sensor may be used to adapt the rate of pacing to correspond to the patient's activity or metabolic need, among other uses.

Communications circuitry is disposed within the housing 401 for facilitating communication between the CRM circuitry and a patient-external device, such as an external programmer or advanced patient management (APM) system. The communications circuitry may also facilitate unidirectional or bidirectional communication with one or more implanted, external, cutaneous, or subcutaneous physiologic or non-physiologic sensors, patient-input devices and/or information systems.

In embodiments that provide cardiac electrical therapy, the therapy device 400 may include circuitry for detecting and treating cardiac tachyarrhythmia via defibrillation therapy and/or anti-tachyarrhythmia pacing (ATP). Configurations providing defibrillation capability may make use of defibrillation coils 441, 442 for delivering high energy shocks to the heart to terminate or mitigate tachyarrhythmia. In some embodiments, the implantable therapy device 400 may include circuitry for selection of pacing electrode(s), timing sequence, and/or amplitude or pulse waveform output configurations (collectively referred to as pacing output configuration) to be applied via one or multiple electrodes within one or multiple heart chambers.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method, comprising:
sensing, within a patient using implantable electrodes, an electrical signal indicative of electrical activity of the patient's heart;
identifying a tachycardia event based on the electrical signal;
sensing, within the patient and during the tachycardia event, a mechanical response signal indicative of a mechanical response of the patient's heart to the tachycardia;
developing a template indicative of the mechanical response of the patient's heart to tachycardia based on the mechanical response signal;
sensing a second mechanical response signal indicative of the mechanical response of the patient's heart to a subsequent tachycardia event;
determining regularity of the second mechanical response signal relative to a threshold established for the patient by comparing the template to the second mechanical response signal;
determining a state of patient hemodynamics during the subsequent tachycardia event based at least in part on the regularity of the second mechanical response signal, wherein determining the state comprises determining whether the subsequent tachycardia event comprises a stable tachyarrhythmia or unstable tachyarrhythmia;
selecting one or more therapies to treat the subsequent tachycardia event based at least in part on the determined state of patient hemodynamics; and
delivering the selected one or more therapies to treat the subsequent tachycardia event, wherein the steps of developing the template, determining the regularity, determining the state of hemodynamics, selecting, and delivering are performed at least in part by circuitry.

2. The method of claim 1, wherein sensing of the mechanical response signal is initiated following a time delay after identifying the tachycardia event to confirm that the tachycardia event is sustained.

3. The method of claim 1, wherein determining the regularity of the second mechanical response signal comprises extracting morphological features from the second mechanical response signal and the template.

4. The method of claim 3, wherein determining the regularity of the second mechanical response signal comprises:
calculating a feature correlation coefficient by comparing the morphological features extracted from the template and the morphological features extracted from the second mechanical response signal for multiple cardiac cycles of the subsequent tachycardia event; and
calculating a variance of the feature correlation coefficient for the multiple cardiac cycles, wherein a relatively larger variance indicates less regularity and a relatively smaller variance indicates greater regularity.

5. The method of claim 1, wherein determining regularity of the mechanical response signal comprises determining regularity of the second mechanical response signal over multiple cardiac cycles of the subsequent tachycardia event.

6. The method of claim 1, wherein selecting the one or more therapies to treat the subsequent tachycardia event comprises selecting between an anti-tachycardia pacing therapy and a cardioversion or defibrillation therapy, wherein the anti-tachycardia pacing therapy is selected if the subsequent tachycardia event is determined to be stable tachycardia and the cardioversion or defibrillation therapy is selected if the subsequent tachycardia event is determined to be unstable tachycardia.

7. The method of claim 1, wherein determining regularity of the second mechanical response signal relative to the threshold comprises comparing a metric indicative of the regularity of the second mechanical response signal to the threshold.

8. The method of claim 1, further comprising determining the threshold for the patient based on the patient's normal sinus rhythm.

9. The method of claim 1, wherein determining the state of patient hemodynamics comprises quantizing the regularity of the mechanical response signal into one of at least three levels comprising high, medium, and low regularity using regularity thresholds between the levels, and wherein high regularity indicates stable hemodynamics, low regularity indicates unstable hemodynamics, and medium regularity indicates blunted hemodynamics.

10. A method, comprising:
identifying an event of tachycardia based on an electrical cardiac signal indicative of electrical activity of a patient's heart;
sensing, within the patient and during the event of tachycardia, a mechanical response signal indicative of a mechanical response of the patient's heart to the tachycardia;
determining a metric indicative of regularity of the mechanical response signal over a plurality of cardiac cycles of the tachycardia event relative to one or more thresholds established for the patient by computing an entropy estimate of the mechanical response signal's regularity;
quantizing the regularity metric into one of a plurality of discrete levels of hemodynamic stability for assessing a state of patient hemodynamics during the tachycardia event; and
determining whether the tachycardia is stable or unstable based on the quantization of the regularity metric, wherein the steps of identifying, determining the metric, quantizing, and determining tachycardia stability are implemented at least in part by circuitry.

11. The method of claim 10, wherein quantizing the regularity metric into one of a plurality of discrete levels of hemodynamic stability comprises quantizing the regularity metric into one of three levels using two regularity thresholds, the three levels representative of very stable hemodynamics, very unstable hemodynamics, and blunted hemodynamics.

12. The method of claim 10, wherein the entropy estimate is computed as a negative natural logarithm of a conditional probability of the mechanical response signal being self-similar.

13. The method of claim 12, wherein the conditional probability ranges between 0 and 1, wherein 1 indicates that the mechanical response signal under investigation is regular and 0 indicates that the mechanical response signal is irregular.

14. The method of claim 10, wherein a larger entropy estimate indicates higher irregularity.

15. The method of claim 10, wherein the entropy estimate is indicative of the conditional probability estimate of the heart rhythm to be predictable or regular.

16. The method of claim 10, wherein the plurality of discrete levels of hemodynamic stability comprises stable and unstable levels, and the regularity metric is quantized into one of stable and unstable levels.

17. The method of claim 10, comprising delivering an anti-tachycardia therapy associated with the level of hemodynamic stability of the patient during the tachycardia event.

18. The method of claim 17, comprising tracking the patient's hemodynamics to assess effectiveness of the anti-tachycardia therapy.

19. An implantable system, comprising:
 an implantable cardiac mechanical sensor configured to produce a signal indicative of a mechanical response of a patient's heart to an event of tachycardia;
 a lead comprising one or more electrodes configured to receive an electrical signal indicative of electrical activity of the patient's heart;
 detection circuitry coupled to the lead;
 energy delivery circuitry coupled to the lead; and
 a processor coupled to the sensor, lead, detection circuitry, and energy delivery circuitry, the processor configured to identify a tachycardia event based on the electrical signal, receive the signal indicative of the mechanical response during the tachycardia event, determine regularity of the signal indicative of the mechanical response over a plurality of cardiac cycles of the tachycardia event relative to a threshold established for the patient by performing singular value decomposition on the signal, and determine a status of patient hemodynamics during the tachycardia event based at least in part on the regularity of the signal by determining whether the tachycardia event is stable tachycardia or unstable tachycardia based on the regularity of the signal, the processor configured to deliver one or more anti-tachycardia therapies associated with the hemodynamic status of the patient.

20. The system of claim 19, wherein a spread of eigenvalues or singular values from the performance of the singular value decomposition on the signal indicates elevated irregularity of cardiac rhythm during the tachycardia event.

21. The system of claim 19, wherein the processor performance of the singular value decomposition on the signal indicates dominance of the major component of the signal.

22. The system of claim 19, wherein the processor is configured to determine the state of patient hemodynamics during the tachycardia event by comparing a metric indicative of regularity of the signal to a threshold developed in relation to a normal sinus rhythm condition of the patient.

23. The system of claim 19, wherein the processor is configured to discriminate between a stable and an unstable state of patient hemodynamics based on regularity of the signal, and to deliver the one or more anti-tachycardia therapies based on stability of patient hemodynamics.

24. The system of claim 19, wherein the sensor comprises at least one of an intracardiac pressure sensor, an intravascular pressure sensor, an accelerometer, a microphone, an impedance sensor configured to sense transthoracic impedance, an impedance sensor configured to sense intracardiac impedance, and an impedance sensor configured to sense intramyocardial impedance.

25. An implantable system, comprising:
 an implantable cardiac mechanical sensor configured to produce a mechanical response signal indicative of a mechanical response of a patient's heart to an event of tachycardia;
 a lead comprising one or more electrodes configured to receive an electrical signal indicative of electrical activity of the patient's heart;
 detection circuitry coupled to the lead;
 energy delivery circuitry coupled to the lead; and
 a processor coupled to the sensor, lead, detection circuitry, and energy delivery circuitry, the processor configured to identify a tachycardia event based on the electrical signal, receive the mechanical response signal indicative of the mechanical response during the tachycardia event, determine regularity of at least a portion of the mechanical response signal that is indicative of the mechanical response of the patient's heart to the tachycardia event over multiple cardiac cycles by determining the width of the dominant spectral peak of the mechanical response signal in the frequency domain, determine a status of patient hemodynamics during the tachycardia event by determining whether the tachycardia event is stable tachycardia or unstable tachycardia based on the regularity of the mechanical response signal, and deliver one or more anti-tachycardia therapies based on the hemodynamic status of the patient.

\* \* \* \* \*